(12) United States Patent
Sharma et al.

(10) Patent No.: US 10,893,757 B2
(45) Date of Patent: Jan. 19, 2021

(54) KANGAROO CARE WEARABLE DEVICE AND METHOD THEREOF

(71) Applicant: Bempu Health Private Limited, Bengaluru (IN)

(72) Inventors: Mona Sharma, Jabalpur (IN); Vidisha Agarwal, Dhanbad (IN); Ratul Narain, Silver Spring, MD (US)

(73) Assignee: Bempu Health Private Limited, Karnataka (IN)

(*) Notice: Subject to any disclaimer, the term of this patent is extended or adjusted under 35 U.S.C. 154(b) by 0 days.

(21) Appl. No.: 16/401,053

(22) Filed: May 1, 2019

(65) Prior Publication Data

US 2019/0335918 A1 Nov. 7, 2019

Related U.S. Application Data

(60) Provisional application No. 62/818,005, filed on Mar. 13, 2019.

(30) Foreign Application Priority Data

May 1, 2018 (IN) .............................. 201841016332

(51) Int. Cl.
*A47D 13/02* (2006.01)
*A61B 5/01* (2006.01)

(52) U.S. Cl.
CPC ................ *A47D 13/02* (2013.01); *A61B 5/01* (2013.01); *A41D 2400/482* (2013.01)

(58) Field of Classification Search
CPC .................................. A47D 13/02; A61B 5/01

USPC ......................................................... 224/160
See application file for complete search history.

(56) References Cited

U.S. PATENT DOCUMENTS

| | | | | |
|---|---|---|---|---|
| 3,481,517 A * | 12/1969 | Aukerman | ........... | A47D 13/025 224/160 |
| 4,009,808 A * | 3/1977 | Sharp | ................... | A47D 13/025 224/160 |
| 4,579,264 A * | 4/1986 | Napolitano | .......... | A47D 13/025 224/158 |
| 6,918,770 B2 | 7/2005 | Odiwo | | |
| 7,766,199 B1 * | 8/2010 | Caperon | .............. | A47D 13/025 224/160 |
| 10,555,620 B2 * | 2/2020 | Gibbons | .............. | A47D 13/025 |
| 10,631,582 B2 * | 4/2020 | Brault | .................... | A41D 1/215 |
| 2002/0011503 A1 * | 1/2002 | Hwang | ................ | A47D 13/025 224/160 |
| 2005/0045674 A1 * | 3/2005 | Rehbein | ............... | A47D 13/025 224/160 |
| 2005/0218168 A1 * | 10/2005 | Chua | .................... | A47D 13/025 224/160 |

(Continued)

FOREIGN PATENT DOCUMENTS

WO 2017008139 A1 1/2017
WO 2018047046 A1 3/2018

*Primary Examiner* — Nathan J Newhouse
*Assistant Examiner* — Lester L Vanterpool
(74) *Attorney, Agent, or Firm* — Morrison & Foerster LLP

(57) ABSTRACT

The present disclosure provides kangaroo care neonatal device and method of applying thereof. The device comprises the sling pouch which holds infant and attached to the main structure of device through zippers and zippers can be easily unzipped to access and position the baby for feeding and reposition back for continuing kangaroo care, without needing to remove the sling or the infant.

14 Claims, 13 Drawing Sheets

(56) References Cited

U.S. PATENT DOCUMENTS

| | | | | |
|---|---|---|---|---|
| 2006/0261104 | A1* | 11/2006 | Zambrzycki | A47D 13/025 224/158 |
| 2008/0149235 | A1* | 6/2008 | Jay | A45C 13/02 150/143 |
| 2009/0101683 | A1* | 4/2009 | Gilboa | A47D 13/025 224/160 |
| 2009/0206116 | A1* | 8/2009 | Grant | A47D 13/025 224/160 |
| 2011/0290831 | A1* | 12/2011 | Wang | A47D 13/025 224/160 |
| 2012/0043359 | A1* | 2/2012 | Bergkvist | A47D 13/025 224/160 |
| 2012/0152987 | A1* | 6/2012 | Beltrame | A47D 13/025 224/158 |
| 2012/0234877 | A1* | 9/2012 | Hiniduma-Lokuge | A47D 13/025 224/159 |
| 2014/0197214 | A1* | 7/2014 | Simmer | A41B 1/08 224/160 |
| 2014/0231473 | A1* | 8/2014 | Bailey | A47D 13/025 224/160 |
| 2014/0253313 | A1* | 9/2014 | Schoenberg | B60N 2/28 340/457 |
| 2014/0283277 | A1 | 9/2014 | Wilhelm | |
| 2016/0120333 | A1* | 5/2016 | Brandner | A47D 13/02 224/158 |
| 2016/0174731 | A1* | 6/2016 | Pulley | A47D 15/005 128/878 |
| 2016/0331151 | A1* | 11/2016 | Miller-Hanna | A47D 13/025 |
| 2018/0235379 | A1* | 8/2018 | Lindeman | A47D 13/025 |
| 2019/0014920 | A1* | 1/2019 | Matsuyama | A47D 13/025 |
| 2020/0060434 | A1* | 2/2020 | Caron | A61B 5/02055 |

* cited by examiner

FIG. 2B
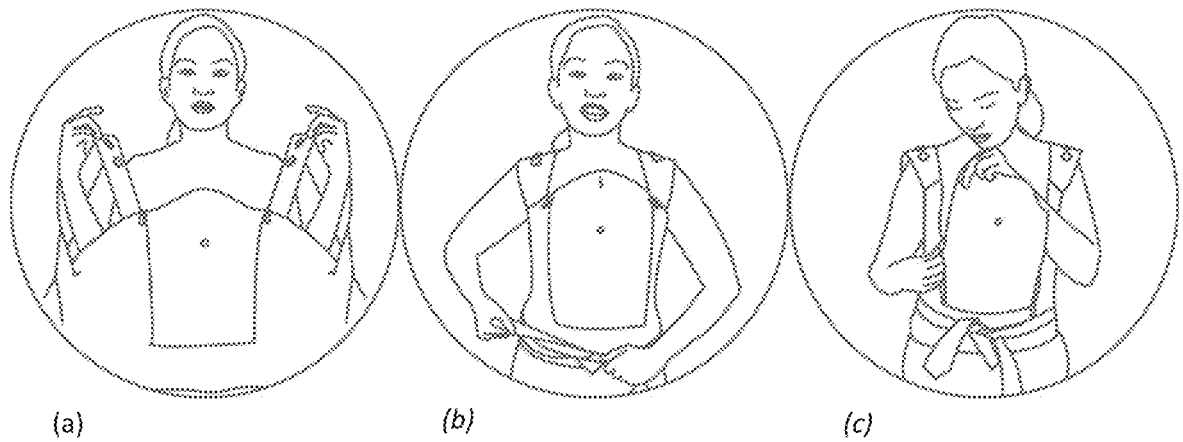
(a) (b) (c)
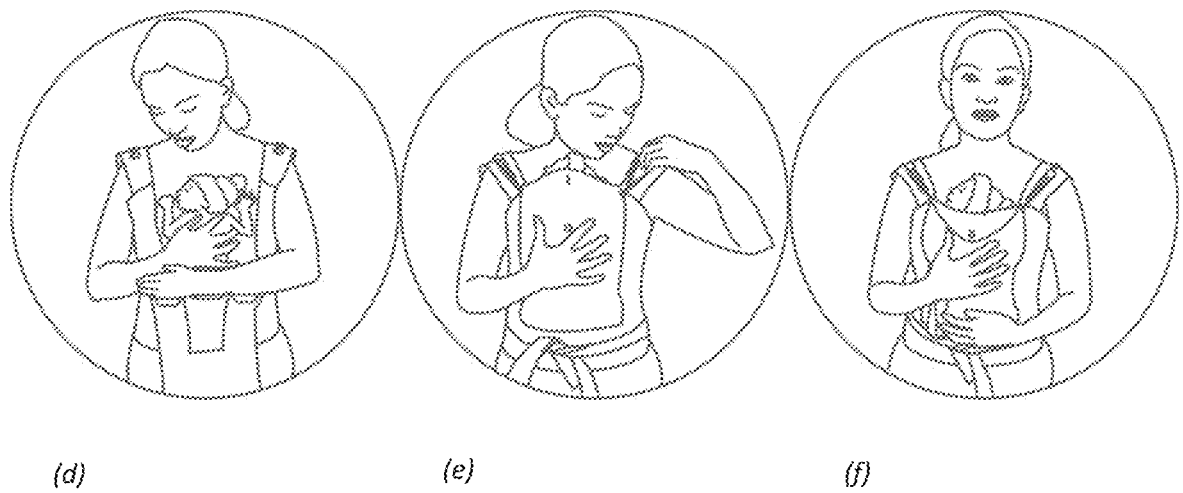
(d) (e) (f)
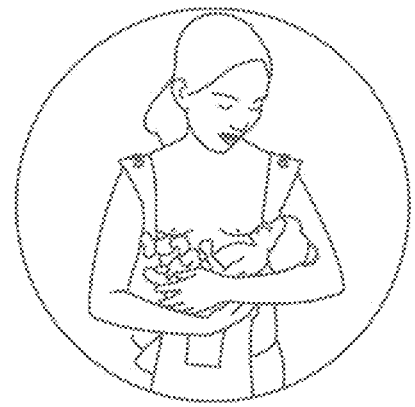
FIG. 3A

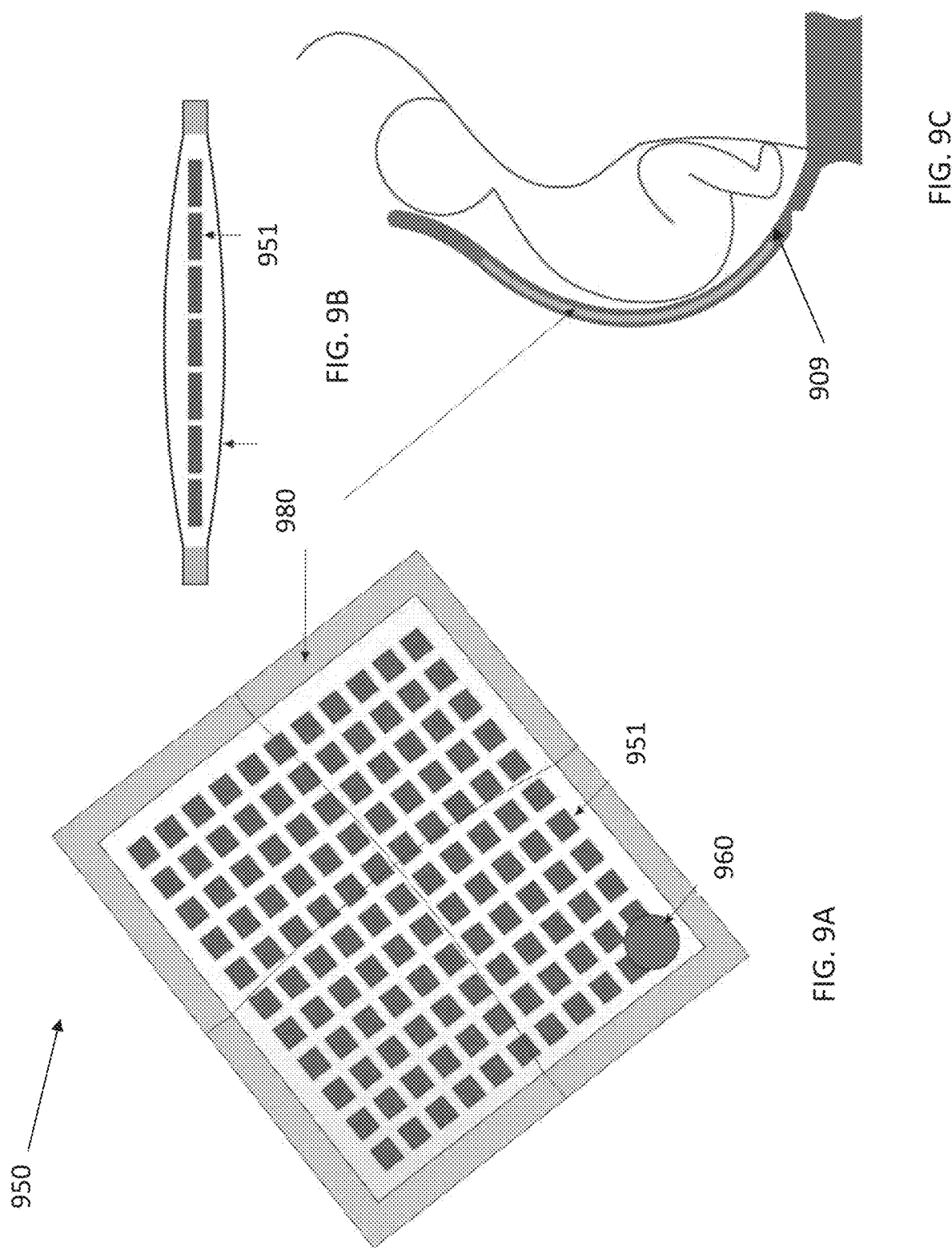

KANGAROO CARE WEARABLE DEVICE AND METHOD THEREOF

CROSS-REFERENCE TO RELATED APPLICATIONS

This application claims the benefit of Indian Provisional Patent Application No. 2018/41016332, filed May 1, 2018 and U.S. Provisional Patent Application No. 62/818,005, filed Mar. 13, 2019; the content of each of which is incorporated herein by reference in its entirety.

FIELD OF THE DISCLOSURE

The present disclosure is in the field of Kangaroo care infant devices. The Disclosure in particular provides a wearable neonatal care device useful for providing the Kangaroo care.

BACKGROUND OF THE DISCLOSURE

The following background discussion includes information that may be useful in understanding the present disclosure. It is not an admission that any of the information provided herein is prior art or relevant to the presently claimed disclosure, or that any publication specifically or implicitly referenced is prior art.

Kangaroo care or kangaroo mother care (KMC) is a technique of newborn care where babies are kept skin-to-skin with a parent, typically their mother. It is most commonly used for low birth-weight and/or preterm babies, who are more likely to suffer from hypothermia, while admitted to a neonatal unit or at home to keep the baby warm and support early breastfeeding. (Reference: Google)

Kangaroo care popularly known as Kangaroo Mother Care (KMC) is a method of newborn care to be used by mothers or any adult caretaker. KMC is an evidence-based practice of care of newborns born preterm or with low weight. KMC practice comprises of two essential key components including 1. continuous and prolonged direct skin to skin contact between the mother & baby and 2. exclusive breastfeeding. While in low-resource settings due to the absence of incubators, it is the only method of newborn care, in better settings it is still an essential method. More importantly, it is recommended to be continued at home after discharge from hospital, till the baby achieves a normal of 2.5 kg and above. Despite known benefits, education and training, KMC is not practiced for the desired durations because of various reasons; the difficulty in providing breastfeeds, holding the baby safe & secure and having hands free to continue with their routine tasks are the few key barriers.

Though there are binders used to hold the baby in KMC position but they are not easy to put on and remove for frequent breastfeeding, require assistance in wearing, does not ensure secure holding of baby in place, and limits the ability of caregiver to continue their routine tasks. All these problems act as barriers to initiate and do prolonged KMC.

Hence, there is a need of a wearable device for Kangaroo mother care which is technically efficient that it does not require assistance in wearing, simultaneously ensuring the secure holding of baby allowing the user/caregiver to be in hands free position and which enables frequent and easy breastfeeding.

Object(s) of the Disclosure

A primary object of the present disclosure is to overcome the drawback/s associated with the prior art thus enabling the caregiver practice prolonged durations of KMC.

Yet another object of the present disclosure is to provide a Kangaroo care wearable device.

Yet another object of the present disclosure is to provide a Kangaroo care wearable device which enables Caregiver to provide frequent and easy breastfeeding.

Yet another object of the present disclosure is to provide a Kangaroo care wearable device with a baby holding pouch which can be zipped open and close to enable breastfeeding and unobstructed placement of the baby.

Yet another object of the present disclosure is to provide a Kangaroo care wearable device with loops on zippers for locking/unlocking the pouch in place preventing accidental falling of baby.

Yet another object of the present disclosure is to provide a Kangaroo care wearable device which requires no wearing assistance.

Yet another object of the present disclosure is to provide a Kangaroo care wearable device which ensures secure holding of baby.

Yet another object of the present disclosure is to provide a Kangaroo care wearable device with Hands free design which allows free mobility of the caregiver.

BRIEF SUMMARY OF THE DISCLOSURE

The Disclosure provides a wearable Kangaroo care Infant device and method thereof.

In an aspect of the present disclosure, there is provided a wearable Kangaroo care Infant device. In embodiments of the present disclosure Kangaroo care device comprising;

a base having a first panel and second panel;

a holding pouch enclosing between the first side of the first panel and first side of the second panel;

a pair of zipper connecting base and holding pouch wherein the zipper are configured to open and close to enable a user to place an infant in the device and secure the infant between the pouch and the caregiver's torso;

a first shoulder strap wherein a first end of the first shoulder strap is connected to the first panel proximate a top portion of the holding pouch and the second end of the first shoulder strap is connected to the first side panel proximate the bottom portion of the holding pouch;

a second shoulder strap wherein a first end of the second shoulder strap is connected to the second side panel proximate the top portion of the holding pouch and the second end of the first shoulder strap is connected to the second side panel proximate the bottom portion of the holding pouch;

a locking loop disposed on the zipper a first fasting means disposed on the shoulder straps wherein the locking loops configured to secure the zipper to the first fasting means a second fasting means configured with the second end of the first panel and second end of the second panel of the base to wrap around the torso of a caregiver a monitoring device disposed in the holding pouch and configured to detect a presence of an infant in the carrier, a feedback unit configured to a user a length of time the infant has been detected in the device In some embodiments the monitoring device and the feedback unit may be a discrete unit that can be used with an existing unit.

In some embodiment the monitoring device monitoring device comprising a first sensor configured to detect a presence of an infant during kangaroo care (KC);

a first circuitry communicatively coupled to the first sensor and configured for receiving a first data associated with the detection of the infant from the first sensor; and a second circuitry communicatively coupled to the first circuitry and configured for receiving a second data from the first circuitry and conveying the second data to a user, wherein the second data is indicative of completion of a KC episode second sensor communicatively coupled to the first circuitry, wherein the second sensor is configured to transmit a fourth data to the first circuitry, wherein the fourth data is indicative of a vital sign of the infant.

In another embodiment the feedback unit comprising an LED array comprising a first region and a second region wherein the first region of the LED device indicates the completion of a total number of KC episode compared to the recommended schedule;

an audio device configured to indicate to a user completion of a KC episode.

In another aspect of the disclosure, there is provided a method of the wearable Kangaroo care Infant device as described above. The method comprises the steps of:
  a) wearing the device by the caregiver as a sling on top part of the body by putting on the shoulders straps (2) on the shoulder and fastening through second fastening means (5) so as to wrap around the torso of a caregiver;
  b) unzipping/opening said zipper means causing the holding pouch (3) to flap down for placing the infant in the support seat means;
  c) flapping up the holding pouch (3) carrying the infant followed by zipping/closing through zipper means by attaching the loops on zippers to said first fastening means for providing greater security;
  d) optionally adjusting the wearable device through height adjustable flap (8) in accordance to the length of infant for providing the kangaroo care.

In some embodiments the disclosure provides the method for monitoring kangaroo care with the device which as described above. The method comprises the following steps:
  a) detecting the presence of an infant using at least one sensor;
  b) communicating a first data indicative of the presence of the infant from the at least one sensor to a first circuitry and comparing the first the first data to a predefined KC with the first circuitry:
  c) determining a second data based on the first data, wherein the second data is indicative of completion of a first kangaroo care episode and wherein the determining a second data comprises the comparing of the first data to a predefined Kangaroo care episode and determining a third data indicative of a total detected KC time;
  d) transmitting the second data from the first circuitry to a second circuitry and third data from the first circuitry to the second circuitry;
  e) indicating at the second circuitry the second data to a user and second circuitry the third data to the user;
  f) Measuring the vital sign from the second sensor;
  g) communicating the vital sign measurement from the second sensor to the first circuitry;
  h) transmitting a third data indicative of the vital sign from the first circuitry to a second circuitry; and
  i) conveying the third data to the user with the second circuitry Further, monitoring device in accordance with the embodiments of the present disclosure encourage family participation in giving KC regularly, making infant care not just a maternal responsibility.

BRIEF DESCRIPTION OF THE DRAWINGS

To further clarify advantages and features of the present disclosure, a more particular description of the disclosure will be rendered by reference to specific embodiments thereof, which is illustrated in the appended drawings. It is appreciated that these drawings depict only typical embodiments of the disclosure and are therefore not to be considered limiting of its scope. The disclosure will be described and explained with additional specificity and detail with the accompanying drawings in which:

FIGS. 2A-2B: a) illustrates flow chart for wearing and using KC wearable device or sling in accordance to an embodiment of the disclosure b) illustrates a user wearing and using KC wearable device or sling in accordance to an embodiment of the disclosure FIGS. 3A-3B: illustrates a) an embodiment showing breast feeding process using KC wearable device b) flowchart depicting breastfeeding during KC in accordance to an embodiment of the disclosure.

FIGS. 9A-9C: illustrate a feedback unit in accordance with the embodiments of the present disclosure.

DETAILED DESCRIPTION OF THE DISCLOSURE

Figure 1:
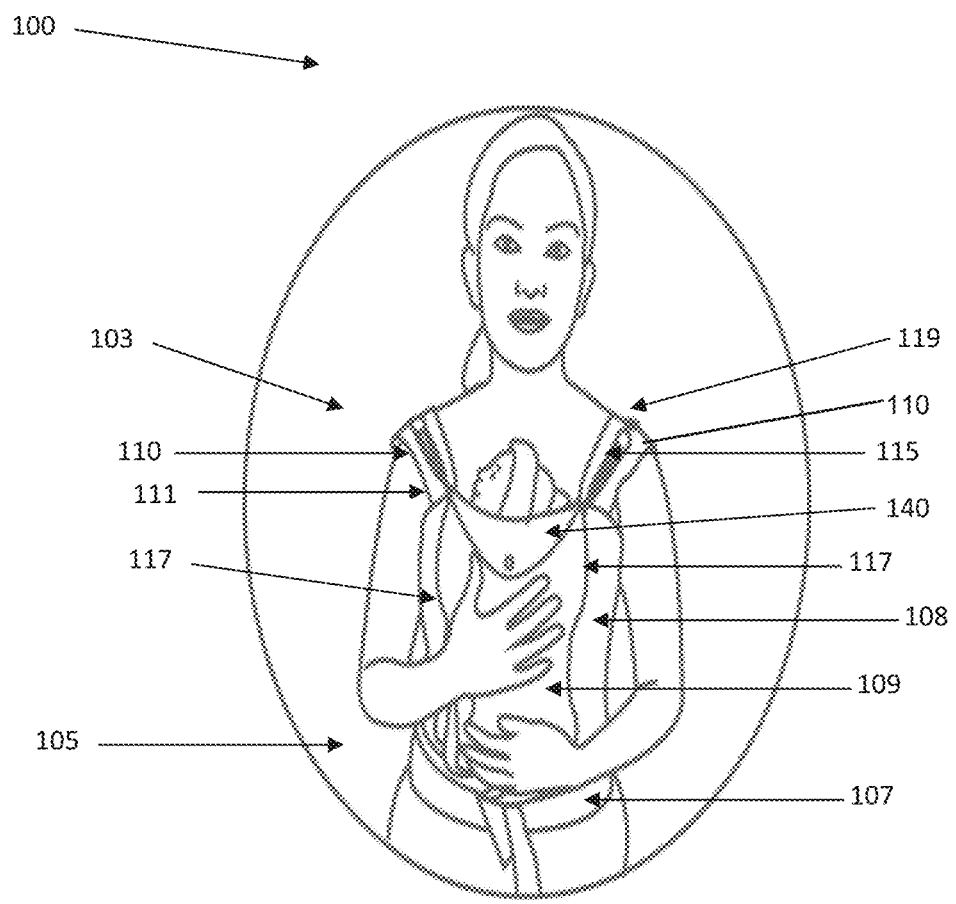
FIG. 1: illustrates an embodiment of the Kangaroo care wearable device and its components.

In the following description of examples, reference is made to the accompanying drawings which form a part hereof, and in which it is shown by way of illustration specific examples that can be practiced.

For the purpose of promoting an understanding of the principles of the disclosure, reference will now be made to the embodiment illustrated in the drawings and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof. Throughout the patent specification, a convention employed is that in the appended drawings, like numerals denote like components.

The disclosure provides a Kangaroo care infant device and in particular provides a wearable neonatal care device useful for providing the Kangaroo care.

The Kangaroo care infant device is useful in a variety of situations and in various ways. Typically, it is used for neonatal kangaroo care. Since the device is easy to use, the wearer can wear the device as a garment on her/his bare chest in the privacy of home prior to a hospital visit. Use of the device is not limited to only premature and low weight babies. This may be useful for older babies or may be used as a baby carrier to support a baby.

The disclosure provides a wearable Kangaroo care Infant device. Referring to FIG. 1 an embodiment of the present disclosure provides a kangaroo care infant device 100 in the form of a sling garment worn on the torso of the body. The device 100 has a base structure having two load bearing shoulder straps 110 with a holding pouch 109. A first fasting means 119 on shoulder straps 110 and second means fasting means 107 is disposed on the bottom portion 105 of the sling 100 below the holding pouch.

In another embodiment, the base of the device is formed of suitable fabrics including, but are not limited to, natural, man-made, and any blend of natural and man-made fibers, for example, micro-suede, cotton, micro-suede/cotton blend, bamboo, ramie, silk, tencel, linen, line/silk blend, linen/cotton blend, polyester/cotton blend, rayon, nylon, polyester, polyester/nylon mesh, elasthane, and the like. In an embodiment, the holding pouch 109 is formed of soft fabrics suitable to be used for infant. Fabrics comprise natural, man-made, and any blend of natural and man-made fibers, or stretchable fabric. In an embodiment, the shoulder straps 110 are formed by fabric or a fabric with elastic means.

The holding pouch 109 has a nappy like structure on the body facing side of the device 100 when worn by a user. The nappy structure supports the seat of the infant to prevent slipping and in some embodiments, includes a liquid absorbing layer to prevent leak. In some embodiments, the nappy structure is disposed near the bottom of the holding pouch 109. In some embodiments, the nappy structure is disposed in a central bottom of the holding pouch 109 but may not span the width.

The holding pouch 109 is attached to the base structure of the device 100 with two zippers 117. In some embodiments the holding pouch 109 is attached to the two load bearing shoulder straps 110 with zipper 117. In some embodiments the holding pouch is attached to the two side panel 108 disposed below the shoulder straps 110. In some embodiments, each zipper 117 includes loops 115 for locking the holding pouch 109 in a closed or zipped up position as shown in FIG. 1. The loops 115 are attached to the zipper pull of zipper 117. The loop 115 is configured to be secured to be button or locking feature 119 disposed on a first end 111 of the each of the two load bearing shoulder straps 110.

Each shoulder straps 110 has at least first fastening means 119 located near the top portion of the device 100. When the zipper 117 pulled up position, the locking loops 115 may be secured by the first fastening means and secured an infant from slipping or accidently falling out from the device. In an embodiment, the load bearing shoulder straps 110 are provided with plurality of first fastening means 119 acting as locking means to connect with said zipper through a loop arrangement for greater security.

The straps 110 and the holding pouch 109 are attached to the second fastening means 107. The second fastening means 107 is disposed at the bottom portion of the device 100. In embodiments the second fastening means is wrap-around belt configured to wrap at least once around the waist of the user. In another embodiment, the base structure is provided with at least a second fastening means 107 adapted to wrap around the torso of a caregiver.

In another embodiment, the second fastening means 107 comprises belt like structure In some embodiments the second fasting means may wrap two or more times around the waist of the user. In another embodiment, the second fastening means is made of material comprising fabric or stretchable fabric to wrap with hands. The second fastening means in another embodiment, is optionally connected with fastening means selected from the group of buckle, belt, buttons, hooks, and clutch.

In some embodiments, the infant holding pouch 109 can be zipped open and close to enable easy and frequent breasting and unobstructed placement of the infant. In some embodiments the holding pouch 109 comprises a height adjustable flap 140 to accommodate infant of different sizes. The adjustable flap 140 adjusts the length of the holding pouch 109.

In an embodiment, the device comprises the sensor (not shown in FIG. 1) to measure the physiological vitals of an infant disposed therein and feedback unit configured with the user.

Figure 2A:
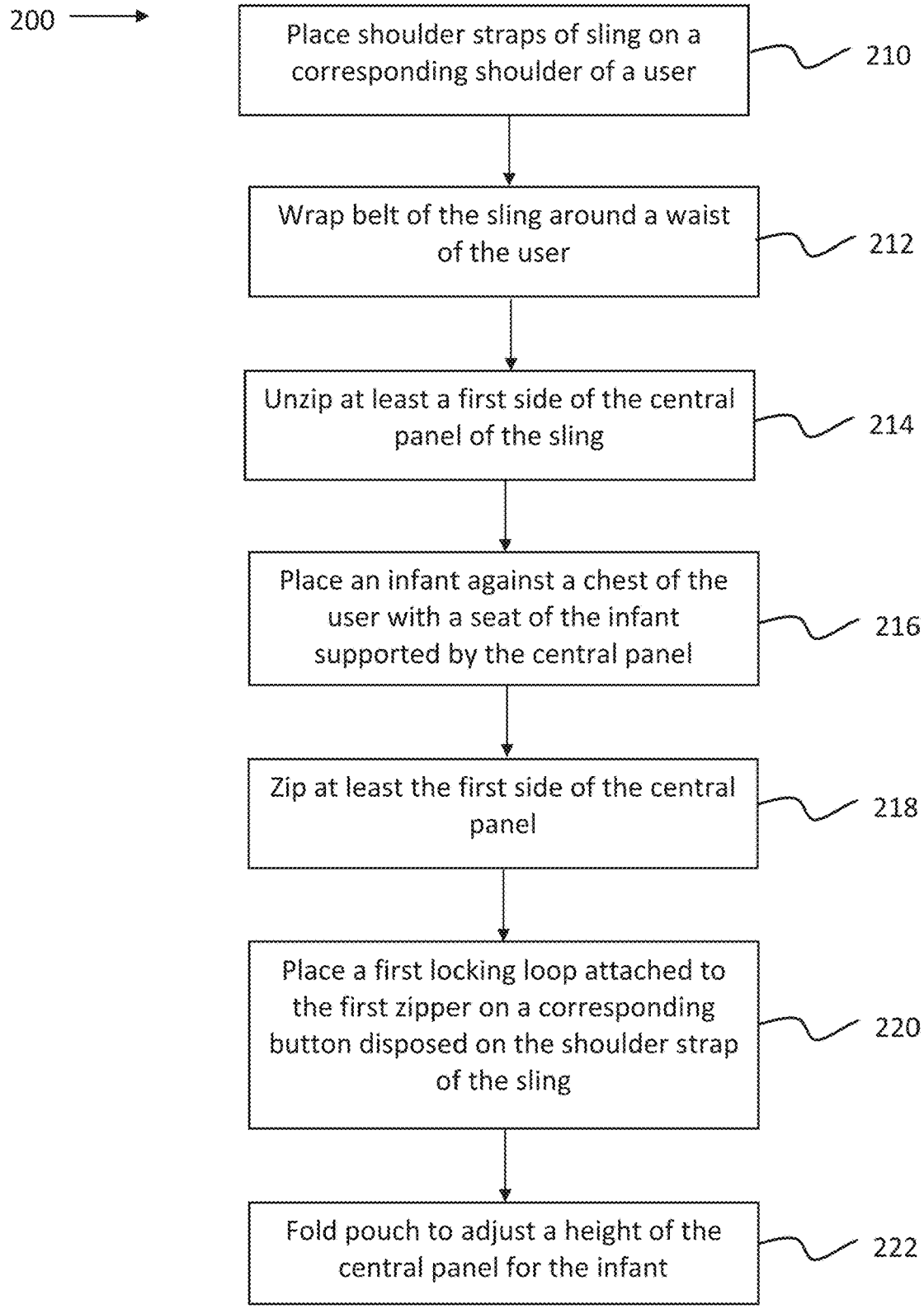

FIG. 2A is a flowchart for wearing and using a KC wearable device or sling in accordance with embodiments of the present disclosure. FIG. 2B illustrate a user wearing and using the KC wearable device. A user wears the sling by placing the shoulder straps of a sling on a corresponding shoulder of the user 210. The user wraps the belt around the waist 212. The user unzips at least a first side of the holding pouch of the sling 214. The user may unzip a second zipper and flap down the central panel to expose the bare chest of the user and receive an infant.

FIG. 2B provides the method for wearing and using the device in accordance with the embodiments of the present disclosure. In an embodiment, the method of the wearable Kangaroo care Infant device comprises following steps:

a) wearing said device by the caregiver as a sling on top part of the body by putting on the shoulders straps 110 on the shoulder and fastening through second fastening means 107 so as to wrap around the torso of a caregiver;

b) unzipping/opening said zipper 117 causing the holding pouch 109 to flap down for placing the infant in the support seat means;

c) flapping up the holding pouch 109 carrying the infant followed by zipping/closing through zipper means by attaching the loops on zippers to said first fastening means 119 for providing greater security;

d) optionally adjusting the wearable device through height adjustable flap 140 in accordance to the length of infant for providing the kangaroo care.

In an embodiment FIG. 3A the method of device while breastfeeding comprises the moving of infant in the holding pouch 109 in such a way that the infant is partially supported by the holding pouch 109 and has access to at least one nipple of a user for breastfeeding. When needing to breastfeed the zippers 117 can be easily unzipped to access and position the baby for feeding and reposition back for continuing KMC, without needing to remove the sling or the baby. This ease of breastfeeding encourages mothers to do prolonged hours of KMC because it does not act as a hindrance to the frequent breastfeeding practice.

Figure 3B:
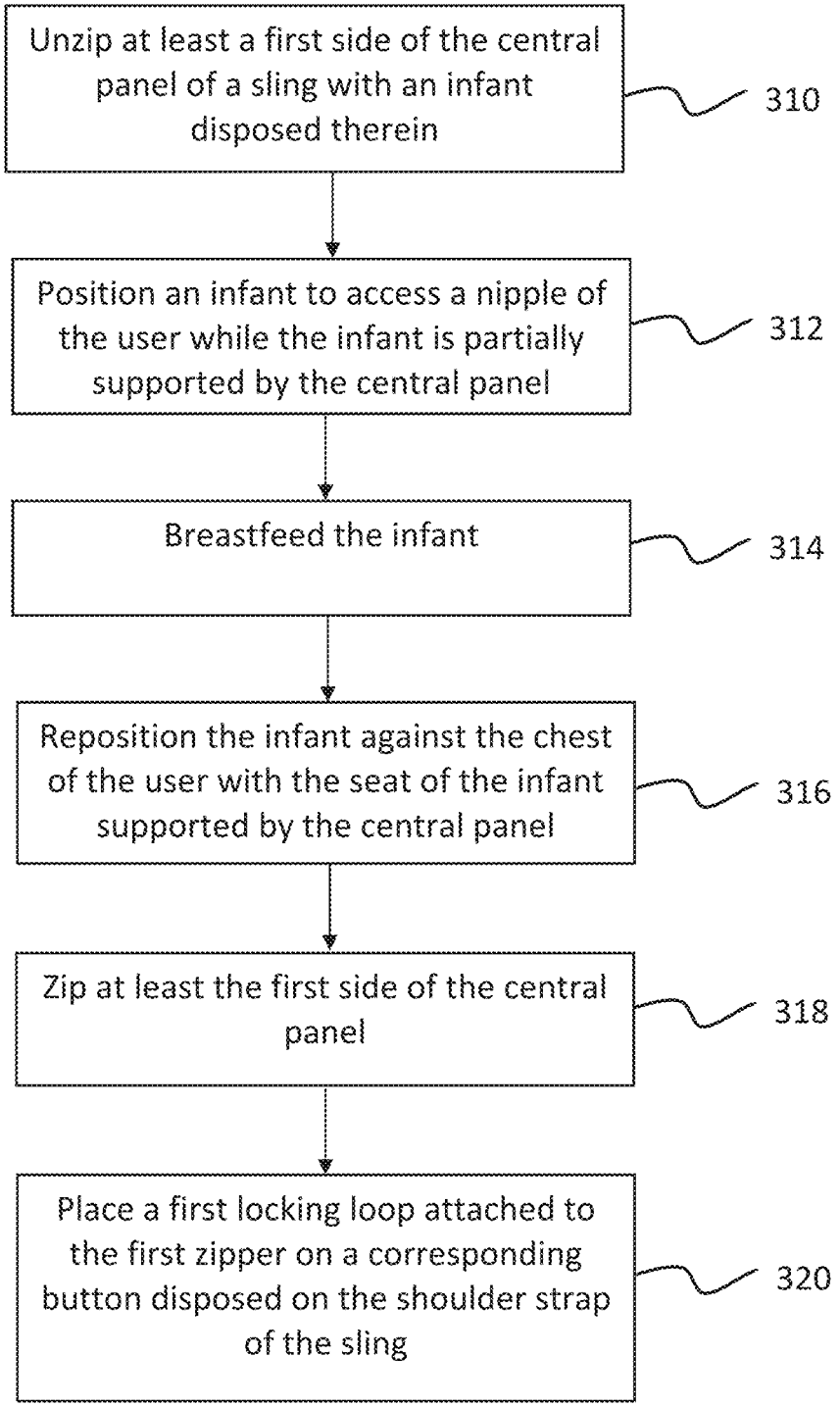

FIG. 3B is a flowchart for using a KC wearable device while breastfeeding. When a user desire to breastfeed an infant therein, the caregiver can open the holding pouch by unzipping the holding pouch 310. The user position the infant for breastfeeding by ensuring the infant can access the nipple of the user 312. In some embodiments the user can position the infant such that the infant is supported by a bottom portion or the central panel. The user can breastfeed the infant 314. Once breastfeeding has concluded, the infant may be repositioned to continue KC 316. For example, the infant may be placed against the chest of the user with the seat of the infant supported by the holding pouch. The holding pouch is then zipped to a closed position 318. The holding pouch may then be locked in place by locking loops over the first fastening means disposed on the shoulder straps of the sling 320.

A Kangaroo care infant device in accordance with the embodiments of the present disclosure has the benefits of frequents and easy breastfeeding, no assistance required for wearing, secure holding and hands free mobility for the care giver to continue with the routine task.

The KC device in accordance with the embodiments of the present disclosure provides with KC sling that does not required assistance from another person. This is achieved through the construction of sling which divides the process of using it in two simple steps. The first step is wearing it as a garment and securing to the body, which can be done all by the caregiver herself. The second step is unzipping the baby pouch, which provides unobstructed access to place the baby and hold with one hand and close the pouch back with the other hand. The nappy supports the seat of baby and allows secure holding without chances of letting the baby slip. There is no other binder/sling which can be used to provide KMC without assistance.

KC device in accordance with the embodiments of the present disclosure provides a user with a KC sling that allows a user to have hands free and can move around safely to continue with routine tasks. This enables the caregiver to do prolonged hours of KMC as desired.

KC Infant Device with Monitoring Device

In some embodiments the KC wearable device is a healthcare product that includes a monitoring device. The monitoring device provides encouragement or motivation to a caregiver to continue providing KC over a period of time. A KC carrier according to embodiments of the disclosure can be used, for example, in a hospital setting, in a home setting, and while a user is commuting or travelling.

A KC carrier and monitoring device according to embodiments of the disclosure can comprise the monitoring device to monitor a length of time a caregiver provides KC, and a feedback unit communicatively coupled to the monitoring device that provides the user with encouragement or motivation while giving KC based on a duration of KC. The monitoring device may also detect body temperature or other vital signs of the infant such as weight, heartbeat, etc., which is conveyed to the user with the feedback unit. The feedback may include visual or audio feedback provided directly from the KC carrier and monitoring system or in some embodiments the monitoring device can communicate with a wireless mobile device such that the wireless mobile device can provide feedback. In some embodiments the monitoring device and feedback unit is configured to attach to an existing KC sling. In some embodiments, the monitoring device and feedback unit is integrated into a KC carrier.

Figure 4A:
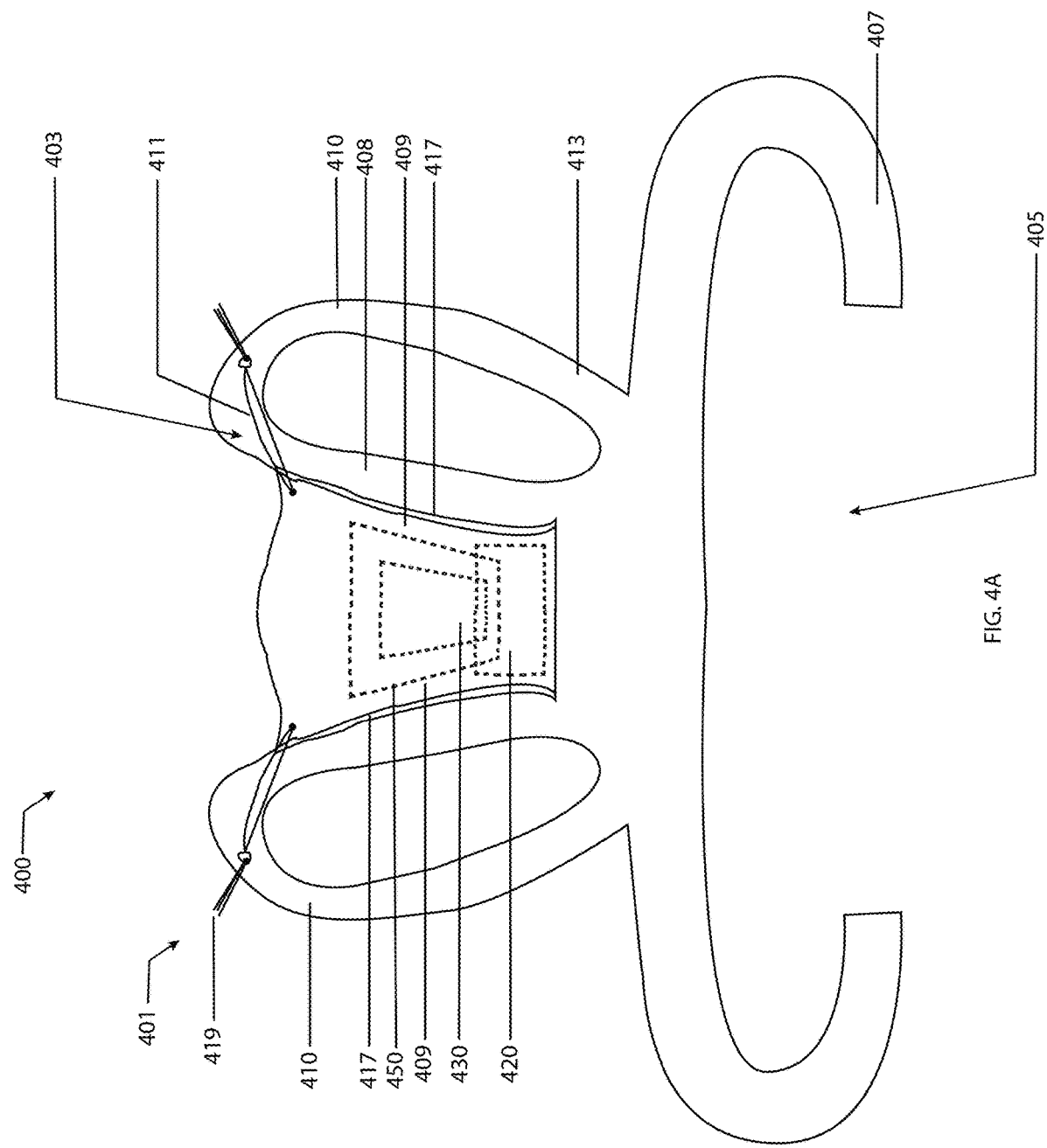
FIG. 4A: illustrates a front view of a KC carrier with monitoring system in accordance with the embodiments of the disclosure.
Figure 4B:
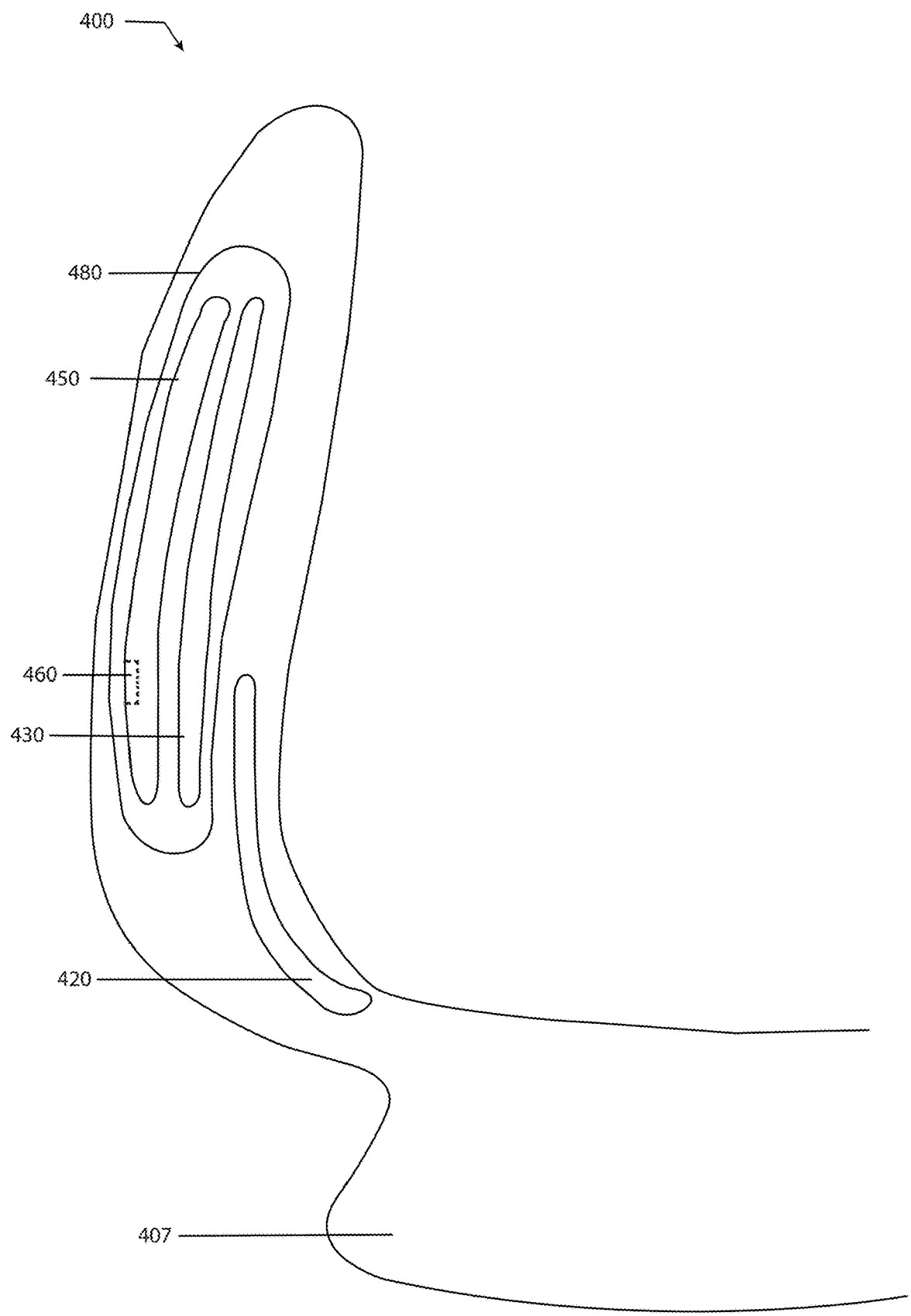
FIG. 4B: illustrates a side view of a KC carrier with monitoring system in accordance with the embodiments of the disclosure.

Referring to the FIG. 4A is a KC carrier 400 in accordance with embodiments of the present disclosure. The KC carrier 400 includes a sling portion 401 and a monitoring device 430. The sling portion 401 includes two load-bearing shoulder straps 410, a holding pouch 409, and a fasting means or belt 407. The monitoring device 430 is disposed in the holding pouch 409 of the sling portion 401. The feedback unit may also be disposed in the holding pouch 409. In some embodiments, the feedback unit may include a mobile device (not shown). As seen in FIG. 4B, the feedback unit may be disposed proximate an outer surface of the holding pouch 409 so that the feedback unit 450 is visible when worn by a user. The monitoring device 430 is disposed between the feedback unit 450 and the nappy portion 420. A waterproof enclosure 480 may enclose the electronics of the monitoring device 430 and the feedback unit 450, e.g., LED display and audio feedback device 460. The waterproof enclosure 480 may be made from a waterproof plastic such as PE or silicone rubber.

Referring to FIG. 4A, the holding pouch 409 is disposed between the two load-bearing straps 410 and is configured to receive an infant and hold the infant against the torso of a caregiver during use. In some embodiments, the holding pouch 409 is disposed between two side panels 408 disposed below the shoulder straps 410. Each load-bearing shoulder strap 410 is disposed on either side of pouch 409, such that a first end 411 of each load bearing strap 410 extends from a top portion 403 of the carrier portion 401 and a second end 413 of each load bearing strap 410 terminates proximate a bottom portion 405 of the carrier portion 401 near belt 407. The belt 407 is configured to tie around a waist of a user, thereby securing the carrier portion 401 to a user.

The pouch 409 is configured to attach and detach (i.e., open and close) from the carrier portion 401. For example in some embodiments, a zipper 417 attaches the pouch 409 to each side panel 408. The zipper 417 provides a simple fastening method that is easy to maneuver with a single hand. This enables a caregiver to easily open and close the holding pouch 409 for frequent breastfeeding and repositioning of the infant after breast feeding for continued KC. One skilled in the art will understand that other fasteners may be used such as Velcro, buttons, and the like, without departing from the scope of this disclosure.

Figure 4C:
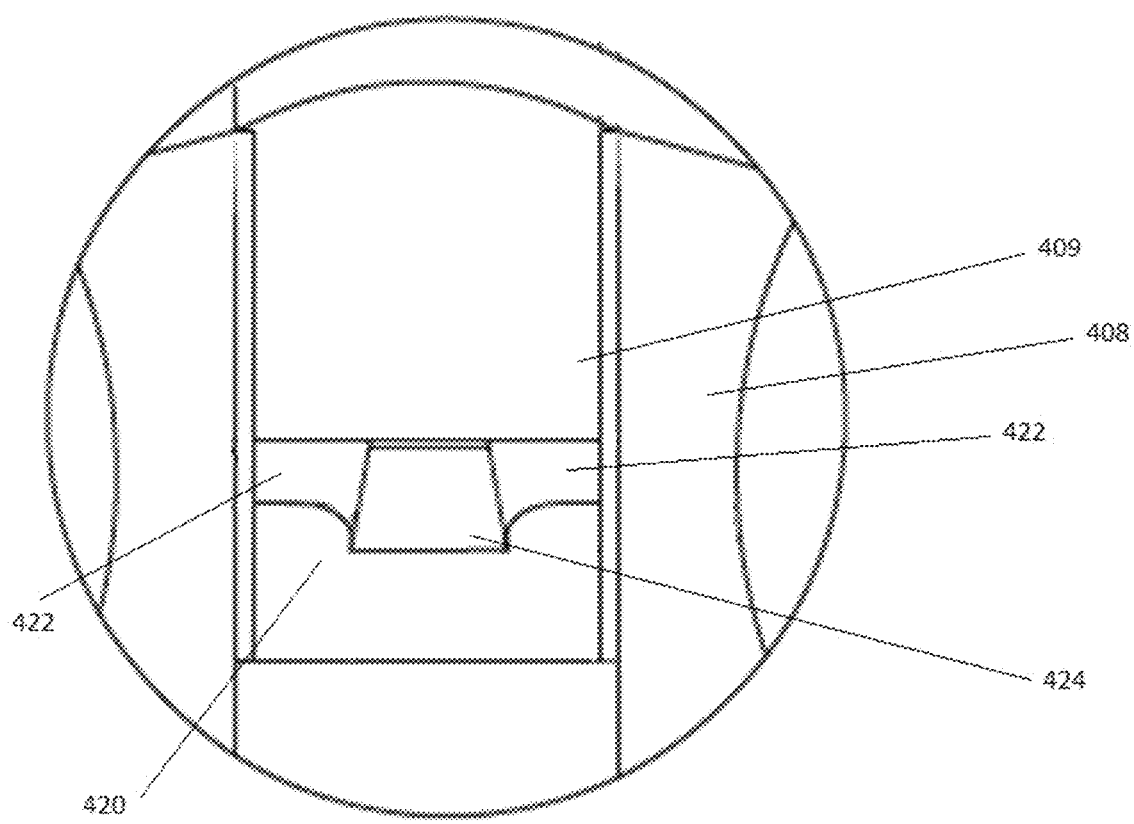
FIG. 4C: illustrates a detailed view of the nappy structure of a KC carrier with monitoring system in accordance with the embodiments of the disclosure.

In some embodiments the pull of the zipper 417 includes a locking loop 415. The locking loop 415 is configured to be secured to a button 419 disposed on a first end 411 of each shoulder strap 410. The locking loop ensures that the zipper 417 does not become undone while an infant is placed in the carrier 401. In some embodiments, the holding pouch 409 includes a nappy structure 420 disposed on the side of the carrier 400 facing the caregiver. The nappy structure 420 is provided to support the seat of the infant and to prevent slipping. The nappy structure may be disposed near the bottom and extend along the width of the pouch 409. In some embodiments, the nappy structure 420 prevents diaper leaks. Specifically, referring to FIG. 4C, the nappy structure includes a wing portion 422 that extends along the width of the pouch 409 and a centre extending portion 424 that protrudes from the wing portion 480. One skilled in the art will understand that details provided with respect to the KC carrier may apply to the KC sling as described above in FIG. 1.

Monitoring Device

Figure 5:
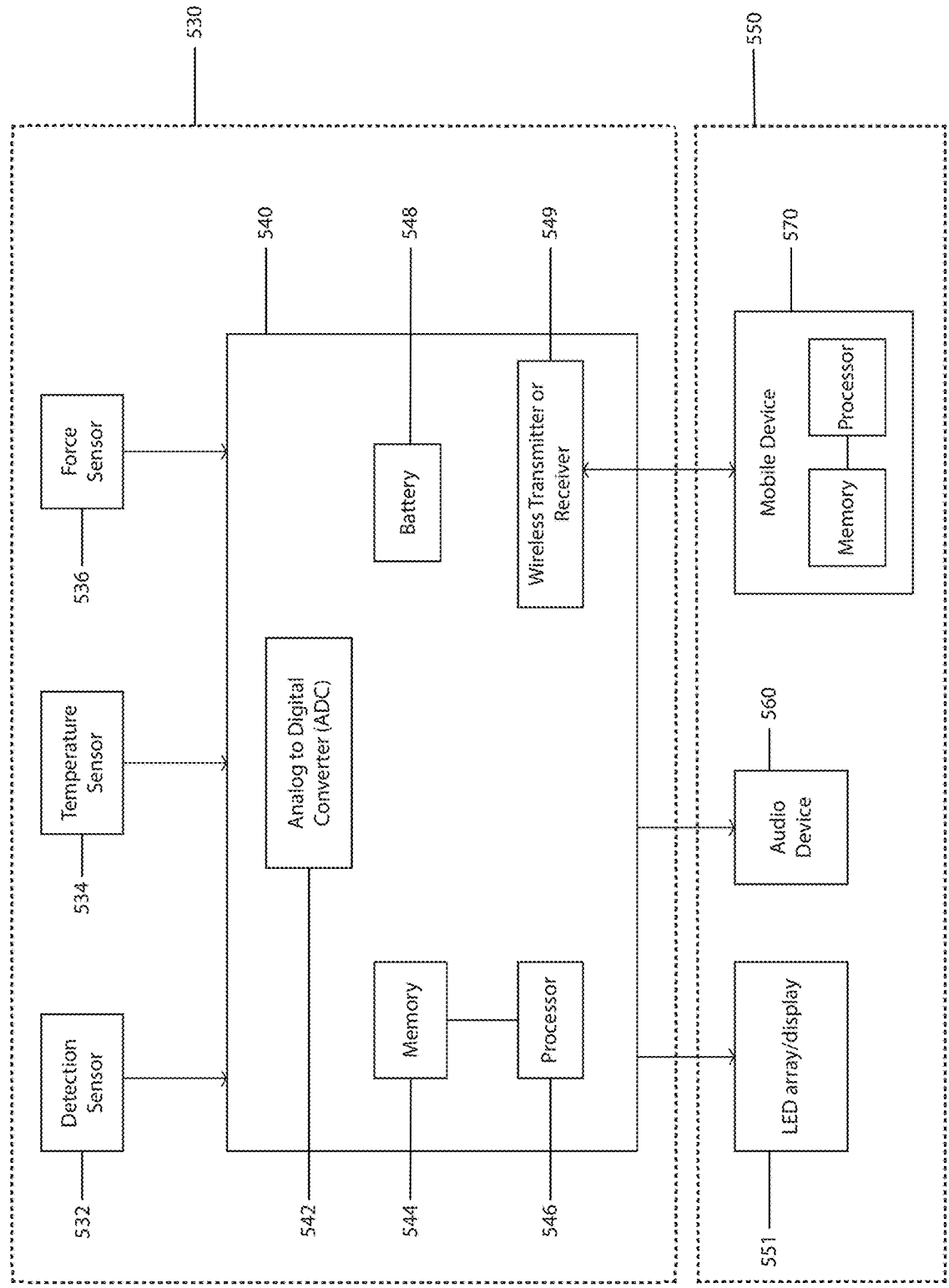
FIG. 5: illustrates a block diagram of an example of an example of monitoring system in accordance with the embodiments of the disclosure.

The KC carrier includes a monitoring device configured to detect the presence of an infant disposed in the KC carrier. FIG. 5 is a block diagram of the circuitry 500 for the KC carrier. The circuitry 500 includes a monitoring device 530 communicatively coupled to feedback unit 550. The monitoring device 530 comprises at least a detection sensor 532 coupled to a control canter 540. In some embodiments the monitoring device 530 includes a plurality of sensors coupled to control center 540. The feedback unit 550 comprises at least one feedback device to provide the user with audio or visual feedback. In some embodiments, the feedback unit comprises a plurality of feedback devices, for example an LED display 551 or an audio device 560. In some embodiments, the feedback unit 550 includes a mobile device 570.

Figure 6C:
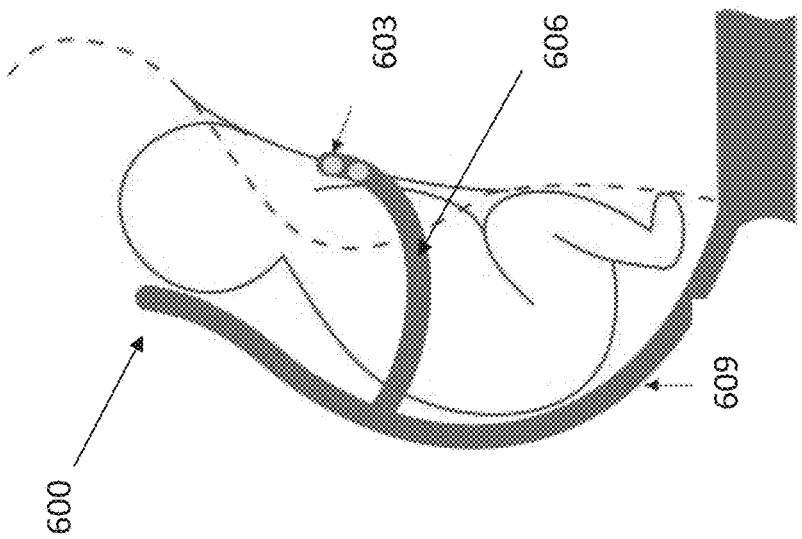
FIGS. 6A-6C: illustrate an exemplary of sensor placement for the monitoring device of the KC carrier according to the example of the disclosure.

The monitoring device 530 includes at least a first detection sensor 532 that is communicatively coupled to the control center 540 of the monitoring device 530. The first detection sensor is used to detect the presence of an infant. In some embodiments, the detection sensor is a force or pressure sensor. When the infant is disposed in the KC carrier, the infant will exert pressure against the pouch due to the weight of the infant, this pressure or force can be detected by the force or pressure sensor. FIG. 6A shows an exemplary arrangement of pressure sensors 601 to detect the presence of in infant in accordance with embodiment of the present disclosure. In some embodiments, the pressure is detected by force or pressure gauges disposed in the shoulder straps of the KC carrier. In some embodiments, the infant is detected with a piezoelectric fabric to detect a mechanical load. When infant is positioned in the KC carrier, the holding pouch becomes taut and the infant puts pressure on the fabric. A corresponding signal is communicated to the control center of the monitoring device.

Figure 6B:
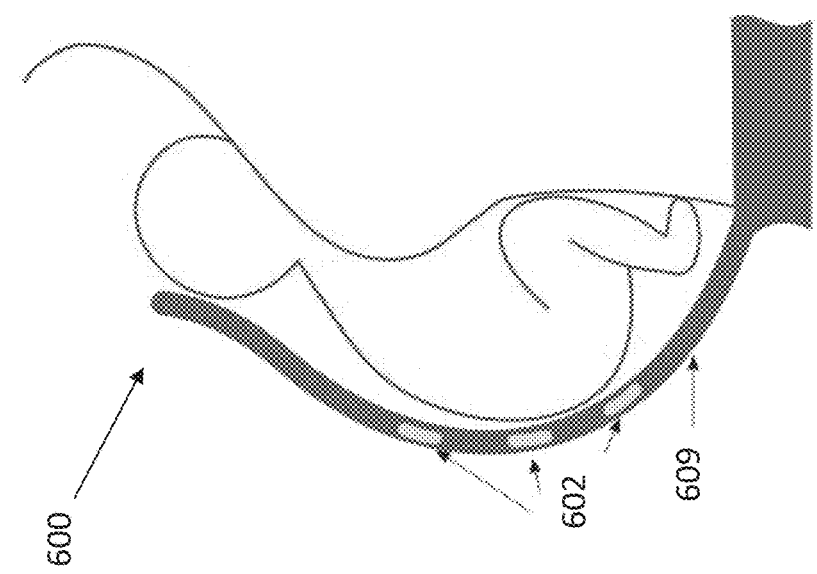
Figure 6A:
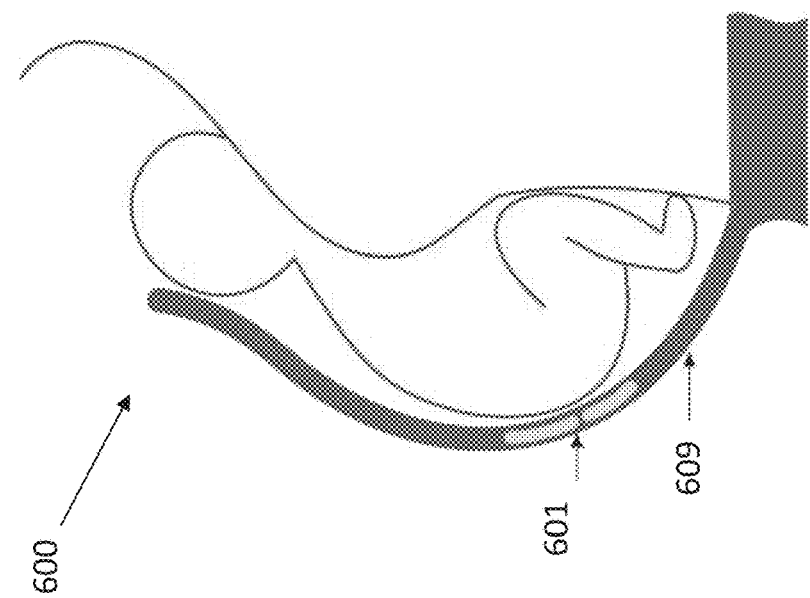

FIG. 6B illustrates using temperature sensors 602 disposed in the holding pouch 609 of the KC carrier 600 to detect an infant. The temperature sensors 602 are positioned in multiple locations of the holding pouch to detect the temperature of the infant to determine the presence of the infant. A corresponding signal is communicated to the control center of the monitoring device. FIG. 6C illustrates capacitive touch sensors 603 used to detect an infant in the KC carrier 600. The capacitive sensors 603 may be placed on an arm 606 of the holding pouch 609. For example, the holding pouch 609 may include an arm 606 or strap that can be placed between the user and infant. When skin is detected on both sides of the capacitive sensor, indicating skin-to-skin contact between the infant and the user, the capacitive sensor sends a corresponding signal to the control center. In some embodiments, a temperature sensor may be disposed in the arm 606 of the holding pouch 609.

Referring back to FIG. 5 the control center 540 can include an analog-to-digital converter (ADC), a memory 544, a processor 546, and a battery 548 for providing power to the control center 540. In some embodiments, the batteries are rechargeable. In other embodiments, the batteries are replaceable. In some embodiments, the control center 549 includes a wireless transmitter or receiver 549 such as a Bluetooth device.

The control center 540 is communicatively coupled to the detection sensor 532. The ADC converts the analog information from the detection sensor 532 to digital form, and stores this digital data into memory 544. One or more algorithms stored in memory 544 can be executed by one or more processors 546 within the control center 540 to determine if an infant is detected in the KC carrier. Another algorithm stored in memory 544 can be executed to measure a current interval length of time that the infant is detected. The current interval can be compared with predetermined KC episode lengths or compared to a recommended schedule of KC.

For example, a predetermined KC episode length may be an hour, thirty minutes, or fifteen minutes. If the current interval length of time (e.g., the amount of time the infant is detected in the current KC carrying session or since the last completed KC interval) equals or exceeds a predetermined KC episode, the control center 540 can log the completed KC episode. The completed episode can be communicated to the user with the feedback unit 550 communicatively coupled to the monitoring device 530. In some embodiments, the completed KC episode can be logged and compared to a recommended schedule of KC. After completing a KC episode, a user's progress toward the recommended schedule can be communicated to the user. For example, the recommended schedule of KC may be 8 episodes a day, e.g., eight hours a day. As completed KC episodes are determined the feedback unit can convey this data to the user, for example, with audio or visual feedback. In some embodiments the monitoring device 530 includes a plurality of sensors to detect vital signs of the infant in addition to detecting a presence of the infant in KC carrier. For example, sensor 534 may be a temperature sensor used to monitor a temperature of the infant. In some embodiments, sensor 536 may be a force sensor used to determine a weight of the infant. In some embodiments, additional sensors may include capacitive sensors used to determine a heart rate or pulse of the infant. The plurality of sensors 534, 536 may be communicatively coupled to the control center 540. A second ADC disposed in the control center 540 may process the signal in a manner described with respect to detection sensor 532. The control center 540 may determine if the vital sign is within a predetermined healthy range. In some embodiments, the temperature, weight, and pulse may be conveyed to the user with feedback unit, for example, with audio or visual feedback.

Feedback Unit

Still referring to FIG. 5, the feedback unit 550 can include a plurality of feedback devices, for example, an LED array 551, and audio device 560 and a mobile device 570. One skilled in the art will understand that any combination of these devices may be used in the feedback unit 550. For example, the feedback unit 550 may comprise only the LED array 551. In other embodiments the feedback unit 550 comprises the LED array 551 and the audio device 560. In other embodiments, the feedback unit 550 comprises the LED array 551 and the mobile device 570. In other embodiments, the feedback unit 550 includes the LED array 551, the audio device 560, and a mobile device 570. One skilled in the art will understand that other feedback devices may be used without departing from the scope of the application, for example, a haptic device for providing haptic feedback. Components of the feedback unit 550 are communicatively coupled to the monitoring device 530, specifically the control center 540.

Figure 7:
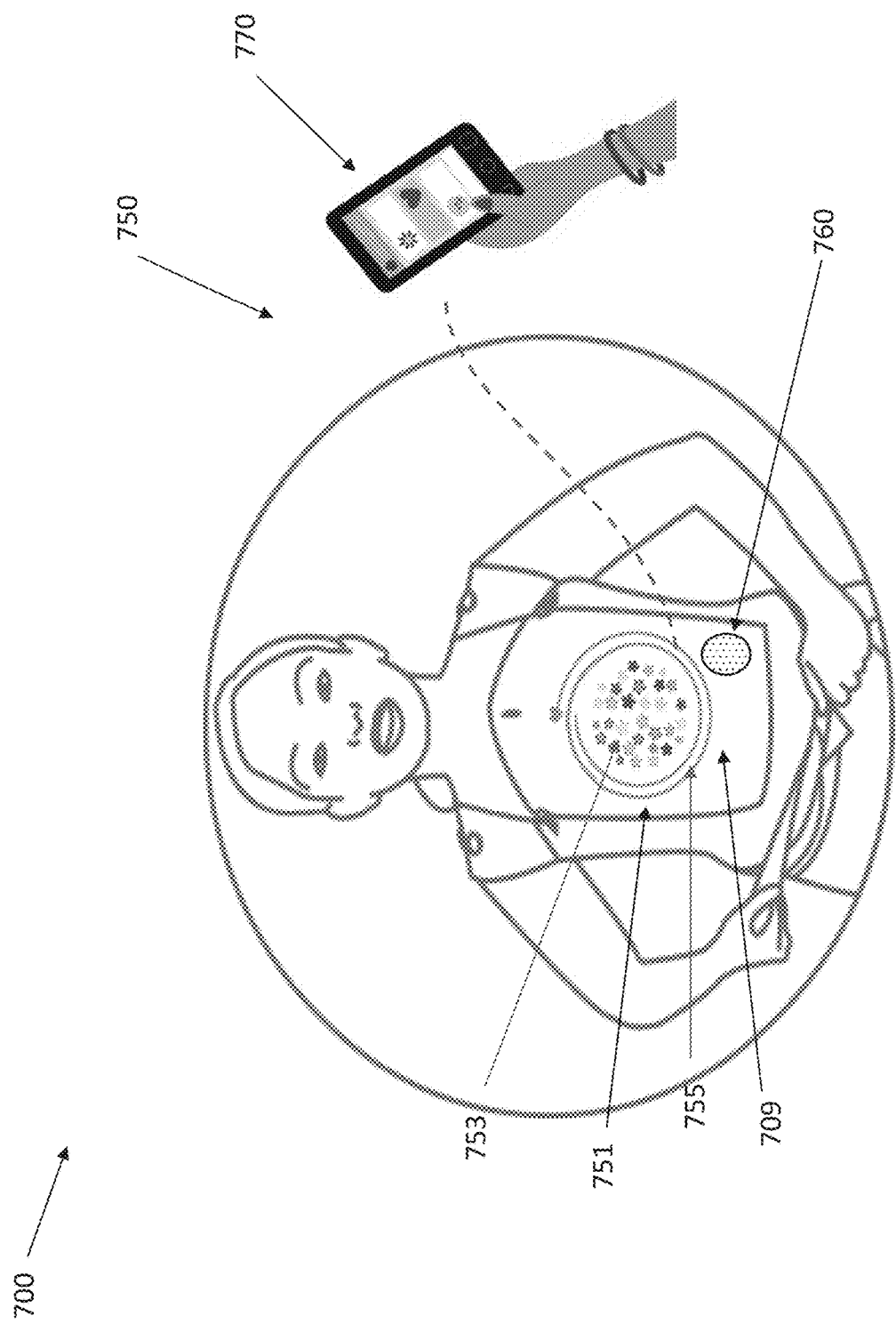
FIG. 7: illustrates an example of a KC carrier worn by the user and remotely connected to a mobile device in accordance with the embodiments of the disclosure.

FIG. 7 is a front view of a KC carrier 700 worn by a user showcasing the feedback unit 750 in accordance with embodiments of the present disclosure. Various components of feedback unit 750 are shown, specifically, a LED display 751 having a first region 753 and a second region 755, an audio device 760, and a mobile device 770. In FIG. 7, feedback unit 750 includes LED display 751 having a first region 753 and a second region 755. One skilled in the art will understand that the LED display 751 may include any number of display regions without departing from the scope of this disclosure.

First region 753 corresponds to providing feedback for a user upon completion of a KC episode. As discussed above, a KC episode is defined as providing KC with KC carrier 700 for a predetermined amount of time, e.g., an hour. Other increments of time to comprise an episode of care may also be used such as thirty minutes or fifteen minutes. As a user completes KC episodes, the first region 753 will illuminate an increasing area, increase the brightness of the first region 753, or change the color of the first region 753 to a brighter hue. In some embodiments, the first region will do a combination of these changes to provide positive reinforcement to the user, e.g., light an increasing area and increase the brightness. In some embodiments, if a user has not been consistent with providing KC with the carrier 700, the illuminated area of 753 may decrease, the color of the display may change from bright to dull, or the brightness of the LEDs may dim.

For example, when the carrier 700 detects the presence of an infant, first region 753 and second region 755 may illuminate. Specifically, the flowers in first region 753 may initially be illuminated as white in color. As the KC episode progresses one by one the flowers may change from white to a bright vibrant color such as red, green, and blue. However if the KC episode is shorter than the predetermined hour like half an hour, the flowers may change to a dull and a grey color from the bright color.

In some embodiments, the second region 755 of LED display indicates the adequacy of KC using carrier 700 according to a predefined amount of time or schedule. For example, the predefined amount of time or schedule may correspond to completing a predetermined number of recommended episodes of KC in a day for a month or 30 day period. Specifically, a predefined schedule may correspond to eight episodes or eight hours of KC with carrier 700 in a day. This would result in approximately two-hundred and forty hours of KC or two-hundred and forty episodes of KC in a month. One skilled in the art will understand that the recommended schedule may correspond to completing more or less than eight episodes or eight hours of KC in a day.

As a user completes an additional KC episode in that month the second region 755 may indicate this progress to the user. In some embodiments the entire second region 755 may be illuminated and portions of the second region 755 may change color, for example, from white to green to indicate progress. In that way the colorful illuminated portion may correspond to the progress, while the white portion may correspond to the number of KC sessions remaining. For example, the memory of the control unit stores the amount of completed KC episodes. Thus, when an infant is detected in the carrier, second region 755 is illuminated from the previous state, i.e., from white to green. As a caretaker performs additional KC episodes, the second region 755 will continue to illuminate and fill the spiral shape. Once the infant is no longer detected in the carrier 700, the display region will shut off. The next instance the infant is detected in the carrier, the second region 755 will be illuminated showing progress from the previous carrying session.

One skilled in the art will understand that the predetermined number of recommended episodes may vary depending on the needs of the user and the length of an episode. One skilled in the art will also understand that the predefined schedule may be longer than a month depending on the needs of the user. For example, the predefined schedule may be a duration of two or three months.

In some embodiments, the LED array may include a third area configured to communicate a vital sign to the user. For example, a temperature, a weight, or a pulse. For example, if the infant is determined to be in a predetermined healthy temperature range a small icon such as a thermometer on the display may be illuminated in green. If the infant is too hot, the thermometer may be illuminated in red. If the infant is too cold, the thermometer may be illuminated in blue. A weight could be indicated with a bar. A full bar could indicate a target weight of 2.5 kgs. When the weight of the infant is determined, it could be displayed as a percentage of the target weight.

Figure 8A:
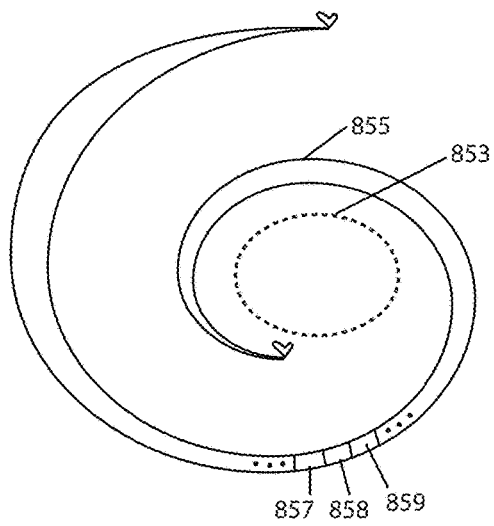
FIGS. 8A-8D: illustrate an example of LED display arrangement in accordance with the embodiments of the present disclosure.
Figure 8B:
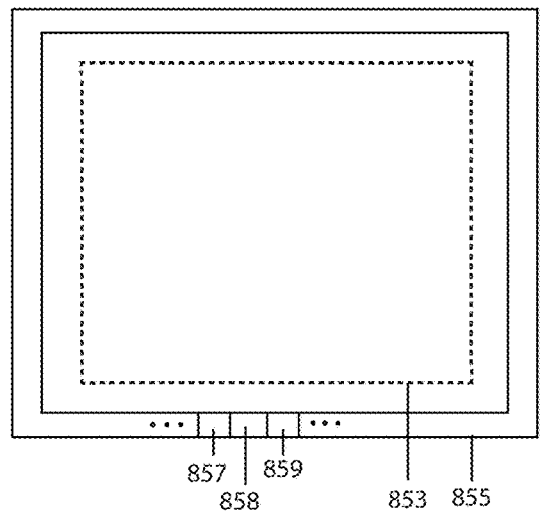
Figure 8C:
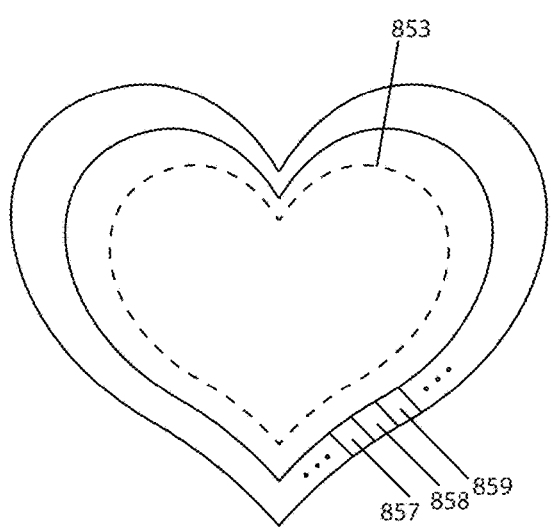
Figure 8D:
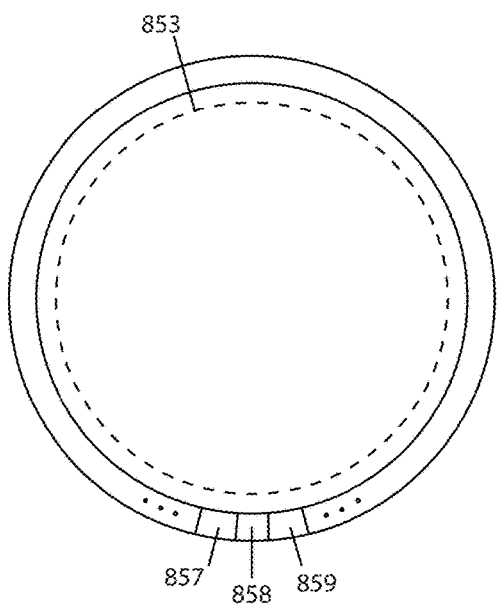

Referring to FIGS. 8A-8D example second regions 853 of feedback unit 850 are shown. The second region 855 may be in the shape of a spiral as shown in FIG. 8A or a perimeter of a shape such as a square as shown in FIG. 8B, circle as shown in FIG. 8D or a non-geometric shapes such as a heart as shown in FIG. 8C, a cloud, or a balloon. In some embodiments, the second region 855 is a spiral disposed around a perimeter of the first region 853.

Referring to FIGS. 8A-8D, the second region 855 may be divided into segments 857, 858, 859, etc. Although only three segments are illustrated, one skilled in the art will understand that the second region 855 may be divided into any number of segments. In some embodiments, each segment corresponds to a recommended KC episode to be completed over a period of time. For example, if the recommended number of KC episodes in a month is two-hundred and forty hours (e.g., 8 episodes a day) the second region 855 is divided into two-hundred and forty discrete segments 857, 858, 859, etc. For each KC episode detected a segment, e.g., segment 857, of the second region is lit. In this manner, the second region 855 conveys to the user a length of time the user has carried the infant with the KC carrier.

In some embodiments the lighting of segments is continuous such that a first KC episode will correspond to segment 857 being illuminated and a second hour of KC will correspond to segment 858 being illuminated. This will result in the second region 855 having a continuous row of lit segments as the user completes KC with the KC carrier. In some embodiments, lighting of segments is reflective of the predetermined schedule. For example, if the predetermined schedule corresponds to two KC episodes in a day and a user performs one KC episode, segment 857 will be illuminated. The following day when the user wears the KC carrier for a second hour, segment 858 will be remain unlit and segment 859 will be illuminated. In this manner, a user may have a visual cue as to the consistency of their KC.

Referring again to FIG. 7, LED display 751 includes a first region 753 comprising a cluster of flowers. In other embodiments, the first region 753 can be customized to be culturally significant. For example, culturally significant animals or nature features such as waves and specific plants. In other embodiments, the first region 753 may be culturally neutral and arranged as a histogram. The examples of specific configurations of the LED display is not intended to limit the disclosure.

FIGS. 9A-9C shows a feedback unit 950 that includes an LED array 951 and speaker 960. Referring to FIGS. 9A-9B, one skilled in the art will understand that LED array 951 may be partitioned into at least a first and second region as described above with respect to FIG. 7. Referring to FIG. 9C, the feedback unit 950 is disposed in the holding pouch 909 of the KC carrier 900. The LED array 951 and the audio speaker 960 may be disposed in a flexible enclosure that is waterproof.

The speaker 960 is configured to provide the user with audio feedback at the conclusion of each KC episode. For example, if a KC episode is an hour, once a user has completed an hour of KC with KC carrier the speaker 960 may play a pre-recorded audio clip. The pre-recorded audio clip may be a song, a pre-recorded message by the user, or a pre-recorded message by a third party. The audio-clip should provide some form of encouragement and provide the user with motivation to continue KC with KC carrier. For example, in some embodiments the audio clip may be a bright song that is culturally relevant to the user. In some embodiments the message by a third party may be encouraging words from the doctor or celebrity.

The feedback unit may include a mobile device include a mobile device as illustrated in FIG. 7. Referring to FIG. 5, the feedback unit 550 may include a mobile device 570 that is configured to wirelessly send and receive data to a wireless transmitter/receiver 549 in control center 540 of the monitoring device 530. For example, the mobile device 570 and the control center 540 may be coupled via Bluetooth or any near field wireless communication methods. The user can then access the KC data transmitted from the monitoring device 530 with an application on the mobile device 570. The application may allow the user to track the user's KC episode pattern as well as vital signs of the infant over time. In some embodiments, through an application, the user has the option to send the data to a medical professional in real time. In some embodiments, through the application, the user has the option to send the data to a third party in real time such as a family member or friend.

Figure 10:
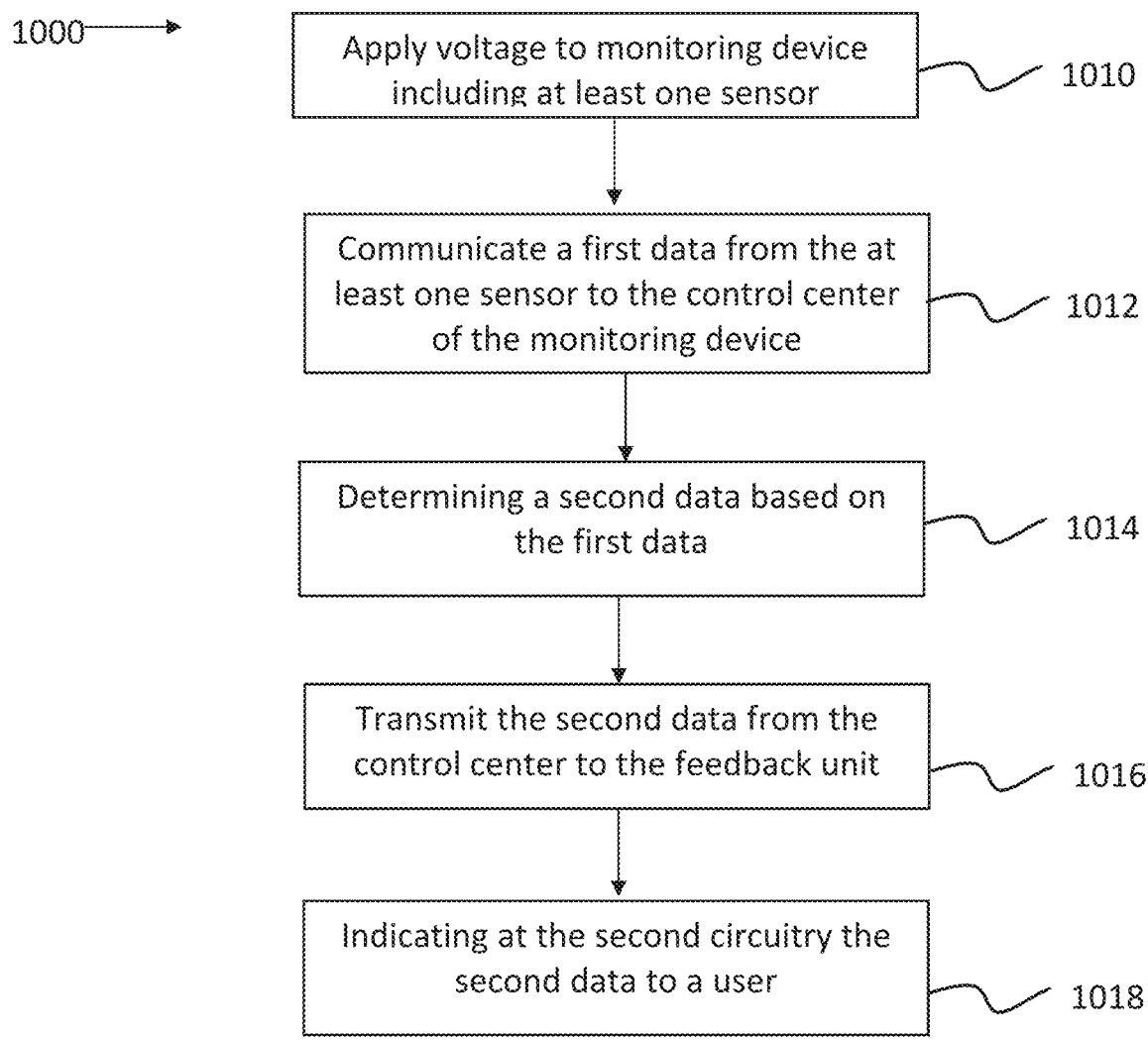
FIG. 10: illustrates flow chart for detecting the presence of an infant using KC carrier in accordance to an embodiment of the disclosure.

In another aspect of the present disclosure, there is provided the method of monitoring kangaroo care with the device. In an embodiments the method comprising the steps of a) detecting the presence of an infant using at least one sensor; and b) communicating a first data indicative of the presence of the infant from the at least one sensor to a first circuitry and comparing the first the first data to a predefined KC with the first circuitry:

c) determining a second data based on the first data, wherein the second data is indicative of completion of a first kangaroo care episode and wherein the determining a second data comprises the comparing of the first data to a predefined Kangaroo care episode and determining a third data indicative of a total detected KC time:

d) transmitting the second data from the first circuitry to a second circuitry and third data from the first circuitry to the second circuitry e) indicating at the second circuitry the second data to a user and second circuitry the third data to the user f) Measuring the vital sign from the second sensor g) communicating the vital sign measurement from the second sensor to the first circuitry;

h) transmitting a third data indicative of the vital sign from the first circuitry to a second circuitry; and i) conveying the third data to the user with the second circuitry FIG. 10 is a flowchart for detecting the presence of an infant using a KC carrier in accordance with embodiments of the present disclosure. First, voltage or current can be applied to at least one sensor in the monitoring device 1010. The at least one sensor may be a detection sensor such as a force sensor, temperature sensor, or the like. The detection sensor will communicate a first data that is indicative of the presence of the infant from the at least one sensor to a first circuitry, for example, a control center 1012. The control center may then determine a second data based on the first data 1014. In some embodiments, the control center may have an ADC to convert the analog data data received from the detection sensor to a digital format. The digital data may be stored in a memory of the control center. In some embodiments the digital data is processed to determine the presence of the infant. If a presence is detected, the data may further be processed to determine if a KC episode is completed. The control center may transmit completion of the KC episode or a similar second data to the feedback unit 1016. The feedback unit may then indicate the second data to the user 1018. For example, the KC episode can be indicated to the user using at least one feedback device. In some embodiments the user will receive visual feedback with an LED display. In some embodiments the user will receive audio feedback from a speaker. In some embodiments, the user will be able to interact with an application on a mobile device to track KC episodes.

In some embodiments the digital data may be further processed to compare the completion of a KC episode to a predetermined schedule. For example, the monitoring device may include a logging algorithm to track a detection of an infant from a first time to a second time and determine the length of a KC session. It then compares this log with a recommended KC schedule. Once the comparison is made, the log can be indicated to the user using at least one feedback device. In some embodiments the user will receive visual feedback with an LED display. In some embodiments the user will receive audio feedback from a speaker. In some embodiments, the user will be able to interact with an application on a mobile device to track KC episodes.

In some embodiments, a second sensor, for example, a force sensor or a temperature sensor, is configured to monitor at least one vital sign of the infant disposed in the KC carrier. The second sensor may be communicatively coupled to the control center and send a data or signal indicative of the vital sign. The control center receives the data and optionally digitizes the data with an ADC and stores the data in the memory. The data is optionally processed to determine the vital sign of the infant. The data can be compared with a predefined data sets of healthy vital signs. A signal or data may be sent from the monitoring device to a feedback unit to indicate to the user the vital sign of the infant. For example, if the infant is determined to be in a healthy range of a vital sign then the LED display may indicate the healthy range. In some embodiments, the vital sign may be transmitted to a mobile device where a user can track the information. In some embodiments the vital sign may be transmitted to a health care provider or another third party in real time.

An infant carrier in accordance with embodiments of the present disclosure may include at least a holding pouch having a belt disposed at a bottom portion, side panels disposed on either side of the pouch, zippers to detachably connect the pouch to the side panels, and a pair of shoulder straps that connect to a top and bottom portion of each of the side panels. The holding pouch is configured to receive and hold an infant against a caregiver's torso. The belt is configured to secure a lower end of the holding pouch to the caregiver. Opening and closing the first and second zippers enable a user to place an infant in the sling and secure the infant between the holding pouch and the caregiver's torso.

In some embodiments the carrier or sling may also include a first locking loop disposed on the first zipper, a second locking loop disposed on the second zipper, a first button disposed on the first end of the shoulder strap, and a second button disposed on the first end of the second shoulder strap. The first locking loop is configured to secure the first zipper to the first button and the second locking loop is configured to secure the second zipper to the second button to maintain the holding pouch in a closed position to prevent the infant from slipping out of the KC sling.

According to embodiments of the present disclosure, a method of using a KC sling may include placing shoulder straps of the KC sling on a first shoulder and second shoulder of a user. A belt of the KC sling may then be wrapped around a waist of the user to secure the carrier in place. A holding pouch of the KC sling may be opened to receive an infant by unzipping at least a first zipper disposed on a first side of the pouch. Next, an infant may be placed in the pouch of the sling against a chest of the user, with a seat of the infant supported by the holding pouch. The pouch of the KC sling may then be closed by zipping the first zipper of the pouch. Finally, the pouch may be locked by placing a locking loop attached to the first zipper on a first fasting means disposed on the first shoulder strap.

According to embodiments of the present disclosure, a method of breastfeeding using a KC sling may include opening a pouch of the KC sling while an infant is disposed therein, by unzipping at least a first zipper disposed on a first side of the holding pouch Next the infant may be moved or repositioned in the holding pouch such that the infant is partially supported by the pouch and has access to at least one nipple of a user. The caretaker may proceed to breastfeed the infant and then the infant may be repositioned in the pouch of the sling against a chest of the user such that a seat of the infant supported by the pouch. The pouch may be closed by zipping the first zipper of the holding pouch. Optionally, the holding pouch may be locked by placing a locking loop attached to the first zipper on a first button disposed on the first shoulder strap.

According to embodiments of the present disclosure, a kangaroo care monitoring device may include a first sensor configured to detect a presence of an infant during kangaroo care (KC), a first circuitry communicatively coupled to the first sensor and configured for receiving a first data associated with the detection of the infant from the first sensor, and a second circuitry communicatively coupled to the first circuitry and configured for receiving a second data from the first circuitry and conveying the second data to a user, wherein the second data is indicative of completion of a KC episode. The KC monitoring device may be incorporated into a KC sling According to some embodiments, the first sensor of the monitoring device is one selected from a group consisting of a force sensor, a capacitive touch sensor, a pressure sensor, a piezoelectric sensor, and a temperature sensor.

According to some embodiments, the second circuitry of the monitoring device may include an LED array comprising a first region, wherein illumination of the first region is determined by the second data. According to some embodiments, the LED array of the monitoring device comprises a second region, wherein illumination of the second region is determined by a third data received by the LED array from the first circuitry.

According to some embodiments, the second circuitry of the monitoring device may include an audio device, wherein activation of the audio device is determined by the second data. According to some embodiments, the second circuitry of the monitoring device may be a mobile device, wherein activation of the mobile device is determined by the second data.

According to some embodiments, the monitoring device may include a second sensor communicatively coupled to the first circuitry, wherein the second sensor is configured to transmit a fourth data to the first circuitry, wherein the fourth data is indicative of a vital sign of the infant.

A method of monitoring kangaroo care according to embodiments of the present disclosure may include detecting a presence of an infant using at least one sensor. The first data indicative of the presence of the infant may be communicated from the at least one sensor to a first circuitry. A second data may be determined based on the first data, wherein the second data is indicative of completion of a first kangaroo care episode. The second data may be transmitted from the first circuitry to a second circuitry. The second data may be indicated at the second circuitry to a user.

According to some embodiments, the determining a second data may further comprise comparing the first data to a predefined KC episode. According to some embodiments, the method may include indicating to a user a total time the user has provided KC care. The method may include comparing the first data to a predefined KC schedule with the first circuitry. Next a third data indicative of a total detected KC time may be determined. The third data may be transmitted from the first circuitry to the second circuitry and indicated to a user at the second circuitry.

According to some embodiments, the indicating at the second circuitry further includes at least one selected from a group consisting of illuminating an increasing area of an LED array, increasing a brightness of the LED array, and changing a display color of the LED array. According to some embodiments, the indicating at the second circuitry further includes activating an audio device. Activating the audio device may include playing an audio clip selected from a group consisting of a song, a pre-recorded message by the user, and a pre-recorded message by a third party. According to some embodiments, the indicating at the second circuitry further includes displaying the second data on a mobile device in real time. Optionally, a length of time the infant has been detected may be transmitted to a healthcare provider or a mobile device of a second user.

According to some embodiments, a method of monitoring kangaroo care may include measuring a vital sign from a second sensor. The vital sign measurement may be communicated from the second sensor to the first circuitry. A third data indicative of the vital sign may be transmitted from the first circuitry to a second circuitry; and conveyed to the user with the second circuitry. The vital sign may be one selected from a temperature, a weight or a pulse of the infant.

The invention claimed is:

1. A wearable kangaroo care infant device comprising:
    a base having a first panel and a second panel;
    a holding pouch disposed between the first panel and the second panel;
    a pair of zippers, comprising a first zipper disposed between the holding pouch and the first panel and a second zipper disposed between the holding pouch and the second panel, wherein the pair of zippers is configured to open and close to enable a caregiver to place an infant in the device and secure the infant between the holding pouch and a torso of the caregiver;
    a first shoulder strap wherein a first end of the first shoulder strap is connected to the first panel proximate a top portion of the holding pouch and a second end of the first shoulder strap is connected to the first panel proximate a bottom portion of the holding pouch;
    a second shoulder strap wherein a first end of the second shoulder strap is connected to the second panel proximate the top portion of the holding pouch and a second end of the second shoulder strap is connected to the second panel proximate the bottom portion of the holding pouch;
locking loops, wherein a first locking loop is disposed on the first zipper and a second locking loop is disposed on the second zipper;
a first fastener disposed on the first end of the first shoulder strap, wherein the first locking loop is configured to secure the first zipper to the first fastener;
a second fastener disposed on the first end of the second shoulder strap, wherein the second locking loop is configured to secure the second zipper to the second fastener;
a third fastener disposed below the bottom portion of the holding pouch and configured to wrap around the torso of the caregiver;
a monitoring device disposed in the holding pouch and configured to detect a presence of the infant in the wearable device; and
a feedback unit disposed on the holding pouch and coupled to the monitoring device, wherein the feedback unit is adapted to display on the wearable device a length of time the infant has been detected in the device.

2. The device as claimed in claim 1, wherein the monitoring device comprises:
a first sensor configured to detect a presence of the infant in the wearable device;
a first circuitry in communication with the first sensor and configured to receive a first data associated with the detection of the infant from the first sensor; and
a second sensor in communication with the first circuitry, wherein the second sensor is configured to transmit a second data to the first circuitry, wherein the second data is indicative of a vital sign of the infant.

3. The device as claimed in claim 2, wherein the first sensor is selected from a force sensor, a capacitive touch sensor, a pressure sensor, a piezoelectric sensor, and a temperature sensor.

4. The device as claimed in claim 1, wherein the feedback unit comprises:
an LED display comprising a first region, wherein the first region of the LED display is adapted to indicate a completed kangaroo care (KC) episode compared to a recommended schedule; and
an audio device configured to indicate to the caregiver completion of a KC episode.

5. The device as claimed in claim 4, wherein the LED display of the feedback unit further comprises a second region, wherein the second region is adapted to indicate a total number of completed KC episodes.

6. The device as claimed in claim 1, wherein the monitoring device is adapted to transmit a signal to a mobile device, wherein the signal is indicative of at least one of completion of a KC episode and completion of a total number of KC episodes.

7. The device as claimed in claim 1, wherein the base and the holding pouch are configured to enable the caregiver to provide skin-to-skin contact between the torso of the caregiver and the infant secured in the holding pouch.

8. A method of using a kangaroo care (KC) device, the method comprising:
wearing the KC device, wherein the wearing comprises:
placing a first shoulder strap of the KC device on a first shoulder of a caregiver;
placing a second shoulder strap of the KC device on a second shoulder of the caregiver; and
fastening the KC device to a torso of the caregiver by wrapping a belt-like fastener around the torso of the caregiver;
opening a holding pouch of the KC device by unzipping a pair of zippers, each zipper disposed on either side of the holding pouch;
placing an infant in the open holding pouch;
closing the holding pouch by zipping up the pair of zippers;
securing the pair of zippers, via a locking loop coupled to each zipper, by attaching each locking loop to a fastener, wherein a first fastener is disposed on a first shoulder strap and a second fastener is disposed on a second shoulder strap;
carrying the infant; and
receiving an indication from the KC device based on an amount of time the caregiver has carried the infant in the KC device, wherein the indication is located on the KC device.

9. The method as claimed in claim 8, further comprising moving the infant in the holding pouch such that the infant is partially supported by the holding pouch and has access to at least one nipple of the caregiver for breastfeeding.

10. The method claimed in claim 8, further comprising: adjusting a height adjustable flap of the wearable device based on a length of infant.

11. The method claimed in claim 8, wherein receiving the indication comprises a seeing a visual indication from an LED display located on the KC device.

12. The method claimed in claim 8, wherein receiving the indication comprises hearing an audio indication from an audio device disposed on the KC device.

13. A method of monitoring kangaroo care comprising:
detecting, via a first sensor of a kangaroo care (KC) device, a presence of an infant supported in a holding pouch of the KC device; and
communicating a first data indicative of the presence of the infant from the at least one sensor to a first circuitry of the KC device;
determining a second data based on the first data, wherein the second data is indicative of an increment of time the infant is supported in the holding pouch of the KC device during a carrying session;
determining a third data, wherein the third data is indicative of a total detected time the infant is supported in the holding pouch of the KC device:
transmitting the second data and the third data from the first circuitry to a display on the KC device;
displaying at the display the second data and the third data;
measuring a vital sign from a second sensor;
transmitting a fourth data from the second sensor indicative of the vital sign to the second circuitry; and
conveying the fourth data with the second circuitry.

14. The method as claimed in claim 13, wherein the vital sign is one selected from a temperature, a weight, and a pulse of the infant.

* * * * *